US010387621B2

United States Patent
McNair (10) Patent No.: US 10,387,621 B2
(45) Date of Patent: Aug. 20, 2019

(54) MATCHING OF VIBRATORY INHALERS TO PATIENT VOCAL TRACT FOR OPTIMIZATION OF PARTICLE DISPERSION

(75) Inventor: Douglas S. McNair, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 1970 days.

(21) Appl. No.: 12/688,593

(22) Filed: Jan. 15, 2010

(65) Prior Publication Data

US 2010/0324417 A1    Dec. 23, 2010

Related U.S. Application Data

(60) Provisional application No. 61/145,364, filed on Jan. 16, 2009.

(51) Int. Cl.
| | | |
|---|---|---|
| *G06F 19/00* | (2018.01) | |
| *A61M 11/00* | (2006.01) | |
| *A61M 15/00* | (2006.01) | |
| *G16H 50/50* | (2018.01) | |

(52) U.S. Cl.
CPC ....... *G06F 19/3462* (2013.01); *A61M 11/001* (2014.02); *A61M 11/005* (2013.01); *G06F 19/00* (2013.01); *A61M 15/0085* (2013.01); *A61M 2205/3375* (2013.01); *A61M 2205/3553* (2013.01); *A61M 2205/3584* (2013.01); *A61M 2205/502* (2013.01); *A61M 2205/505* (2013.01); *A61M 2205/6009* (2013.01); *A61M 2210/065* (2013.01); *A61M 2210/1028* (2013.01); *A61M 2230/00* (2013.01); *G16H 50/50* (2018.01)

(58) Field of Classification Search
CPC ....... A61B 8/00; G06F 19/3462; G06F 19/00; A61M 11/001; A61M 11/005; A61M 2210/1028; A61M 2210/065; A61M 2205/505; A61M 2205/3581; A61M 2205/6009; A61M 2205/502; A61M 2205/3375; A61M 2205/3553; A61M 15/0085; A61M 2230/00; G16H 50/50
USPC .................................................. 600/407, 437
See application file for complete search history.

(56) References Cited

U.S. PATENT DOCUMENTS

| | | | |
|---|---|---|---|
| 2007/0225587 A1* | 9/2007 | Burnell et al. | ................ 600/407 |
| 2009/0126731 A1* | 5/2009 | Dunsmore | ........ A61M 16/0096 |
| | | | 128/203.12 |
| 2012/0116238 A1* | 5/2012 | Brand | ...................... A61B 5/08 |
| | | | 600/508 |

* cited by examiner

*Primary Examiner* — Peter Luong
(74) *Attorney, Agent, or Firm* — Shook, Hardy & Bacon L.L.P.

(57) ABSTRACT

An optimization methodology is employed to match vibratory inhaler devices having certain characteristics to the particular anatomical and acoustic properties of a patient's vocal tract, in order to achieve the most effective dispersion of a dry powder medicament using inspiratory effort of a user of the inhaler. In embodiments, optimization involves employing one or more measurements of acoustic frequency spectrum properties as well as one or more anatomical/geometric measurements of the structures comprising the particular patient's mouth, pharynx, and upper respiratory tract and matching a vibratory inhalation device that corresponds thereto.

14 Claims, 7 Drawing Sheets

602 — DOE, JOHN  DOB: 11/5/1966  EMR: 00000974  FIN #: 000000991
AGE: 42 YEARS  GENDER: MALE  LOC: 4 NORTH – ICU; 407;

DISCERN ADVISOR – DPI

🏠 🗎 🗐 📄 🔍 ✎ | 150% ▾ | ● ● ● 🔳

*DISCERN ADVISOR – SPIROMETRY – ACOUSTIC REFLECTORMETRY-BASED DPI ADVISOR*
*PLEASE COMPLETE ALL OF THE FOLLOWING TO DETERMINE DPL*

| CRITERIA | CLINICAL INFORMATION |
|---|---|
| AGE (YR) | 42 |
| GENDER | MALE |
| HEIGHT (CM) | 160 |
| SPIROMETRY | |
| FEV1 | 3.41 |
| FVC | 3.3 |
| FEV1%FVC | 72.3  % |
| ACOUSTIC REFLECTOMETRY | |
| LMIN (CM) | 5.5 |
| LGLOT (CM) | 15.1 |
| AMAX (CM2) | 8.0 |
| RECOMMENDED DPI | 2 |

[DOCUMENT]

[RESET]

🖨 PRINT  ⟳ 5 MINUTES AGO 604 (bracket grouping clinical inputs)
606 (pointing to RECOMMENDED DPI)

FIG. 6

MATCHING OF VIBRATORY INHALERS TO PATIENT VOCAL TRACT FOR OPTIMIZATION OF PARTICLE DISPERSION

CROSS-REFERENCE TO RELATED APPLICATIONS

This application claims the benefit of U.S. Provisional Application No. 61/145,364, filed Jan. 16, 2009, which is herein incorporated by reference in its entirety.

BACKGROUND

The human respiratory tract has an extensive blood supply and its total surface area is about 75-140 square meters in adults, features which make it attractive as a route for administering medicaments (drugs). Local administration of drugs intended to target pulmonary sites of action, as in asthma or chronic obstructive pulmonary disease (COPD), is the traditional application for drug delivery by the respiratory route. However, systemic administration of drugs through the lungs is also attractive for substances that undergo metabolic breakdown in the gastrointestinal tract and are unsuitable for oral administration. Large molecules, such as peptides and proteins, that cannot pass the absorbing membrane after oral administration (insulin as one example) are potential substances for which pulmonary route of administration may be preferable to other routes. Additionally, drugs that undergo extensive 'first-pass' metabolism in the liver may be better to administer via the pulmonary route. The lungs have inherent anatomical and physiological advantages for administration of such drugs. The lungs are robust organs that provide a large (75-140 $m^2$) and well-perfused alveolar surface for absorption with a thin alveolar-capillary barrier and only modest regional variation in the amount of mucus production. Most of the lungs' surface area resides in the alveolated regions of the deep lung, which also contains a rich capillary network to assure efficient gas exchange during the breathing process. There is a lack of mucociliary clearance at the alveolar region so that drug that is deposited in the deep lung is not likely to be expelled and is likely to be absorbed into the bloodstream. The lungs also lack certain peptidases that are present in the gastrointestinal tract, so that bioavailability of peptide or protein drugs may approach that for parenteral routes of administration.

As with other drug delivery routes that are alternatives to oral administration, there are potential challenges to be overcome with drugs being delivered through the lungs. This is because of the number of factors that can strongly influence the efficacy of drug delivery via the pulmonary system, including: particle size, particle density, particle surface morphology, particle charge, hygroscopicity of the particles, rate of dissolution of particles at the site of deposition, the patient's breathing pattern (especially the inspiratory flow rate and the extent of inhalation; slow and deep inhalation tend to increase alveolar deposition), patient comorbidities (such as interstitial lung disease or airflow obstruction), losses within the device or the environment, as well as other factors. Among these factors, particle size distribution is arguably the most critical. The optimal particle size (aerodynamic diameter) for deep (alveolar) pulmonary deposition of particles is around 1-3 μm in diameter. Larger particles become lodged in the upper respiratory tract. Particles smaller than about 0.5 μm tend to be exhaled and not deposited in the respiratory tract at all. In this connection, it is important to note that the size distribution of inhaled aerosolized drug particles is not a constant, as-manufactured size distribution. The sizes of particles in the aerosol plume change continuously during the course of the patient's inhaled 'puff' (inspiratory maneuver), due to a variety of physical processes such as agglomeration (coagulation) through collisions with other inhaled particles, condensation of water vapor on the particles, evaporation in the case of liquid particles, and so forth.

The main challenge in the design of formulations to be delivered to the lungs is the incorporation of the drug in particles with an appropriate aerodynamic size distribution. Past research efforts investigated the deposition profiles for an inhaled nebulizer cloud as predicted from model which assume oral breathing and healthy subjects. For example, some studies determined that oropharyngeal deposition decreases with decreasing median particle diameter, falling from 60% of the inhaled dose at 10 μm to almost 0% below 1 μm. Central airway deposition peaks at 5-7 μm and peripheral airway deposition at 2-3 μm. However, it must be considered that usually the patient's respiratory system status in disease is an important factor that affects directly the behavior of the particles once inhaled. As previously mentioned, particles smaller than 0.5 μm are frequently not deposited in the respiratory tract but are exhaled.

The aerodynamic diameter refers not only to the geometric particle diameter, but also to the particle mass density. Larger but porous particles have been also proposed as an option for reducing inertial impaction of particles onto surfaces in the throat, thereby improving the chance that the particles will reach the alveolar region. However, large, porous particles have large surface area and, in general, are more susceptible to condensation of water vapor from the humid airstream during their progress through the respiratory flow path. In the case of highly hygroscopic particles, this can not only lead to increases in particle size but also increases in particle density.

As the aerosol plume passes from the inhaler device into the patient's airways, the particle size may change by evaporation of the volatile components (solvents) on the surface of inhaled liquid droplets, by condensation of water vapor from the humid airways upon the inhaled droplets or powder particles, and by agglomeration of particles that collide with one another during transit. The transit time during the inspiratory maneuver by which the aerosol plume is inhaled into the patient's respiratory tract has a duration of hundreds of milliseconds or longer. The particle size distribution changes in the particle plume during this time may be substantial. In many cases, the mean particle size may increase by a factor of two or more, by processes of particle-particle collisions and agglomeration (coagulation). The larger particles undergo greater inertial impaction on mouth and oropharynx and other structures of the upper respiratory tract or are precipitated and settle within the inhaler device itself. Therefore, the development of effective pulmonary delivery systems that can reach the alveoli is still a challenge. Furthermore, the interaction of the aerosol plume may be significantly influenced by respiratory physiology, inspiratory airflow parameters, and attributes of a patient's upper airway anatomy. In particular, aerosolization mechanisms that involve vibratory elements that emit acoustic frequencies at audible and ultrasonic frequencies may either accelerate or inhibit particle agglomeration, depending on these attributes.

The generation of clouds of droplets by means of acoustic waves was first reported in 1927. Two different mechanisms explain atomization, capillary waves and, in the case of ultrasonic frequencies, cavitation. The Kelvin equation for capillary waves is described as:

$$\lambda = \left(\frac{2\pi\sigma}{\rho f^2}\right)^{1/3}$$

where:
λ=Wavelength of surface waves at the air/liquid interface
σ=Surface tension coefficient
ρ=Liquid density
f=Frequency of the surface waves After further investigations, the Kelvin equation was later modified and the following expression derived:

$$\lambda = \left(\frac{8\pi\sigma}{\rho F^2}\right)^{1/3}$$

where F is the forcing sound frequency or frequency of the acoustic signal. These theoretical bases were already established when in 1927 the possibility of atomizing liquid by exciting them with ultrasonic waves was described. Decades later, it was determined that the expression relating the wavelength to droplet size D could be through an empirical constant, which was experimentally reported to be 0.34.

$$D = 0.34\left(\frac{8\pi\sigma}{\rho F^2}\right)^{1/3}$$

Based on this principle, nebulizer devices currently in the market operate at relatively high frequencies (usually 20 to 200 KHz) aiming to impart energy to the liquid efficiently to generate small droplet size distributions, while formulations to be nebulized under this principle should have higher densities and lower surface tension values in order to achieve lower droplet diameters. Likewise, vibratory dry power inhaler (DPI) devices tend also to operate at relatively high frequencies (usually greater than 2 KHz) aiming to transfer energy efficiently to the powder to cause deagglomeration and nearly complete dispersal of the solid powder into a plume having a small particle size distribution capable of achieving extensive alveolar deposition.

Some dry powder inhalers and nebulizer devices employ vibratory means to disperse an amount of a drug powder into an aerosol that is carried on the stream of inspired air as an aerosol 'plume' (referred to herein as "vibratory inhalers"). With vibratory inhalers, acoustical vibrations created by the dispersal elements have a frequency spectrum that generally interacts with the acoustic properties of the patient's mouth, pharynx, and upper airway. The transit time for air between the inner aspect of the teeth to the upper aspect of the vocal folds is sufficiently long that significant coagulation of powder particles can occur en route. If the frequency spectrum of the vibratory inhaler device is matched to the acoustic properties of the patient's upper respiratory flow-path, the acoustic vibrations emitted by the vibratory dispersal element may substantially inhibit the undesired coagulation and precipitation and/or impaction upon the surfaces of these upper structures, permitting more of the powdered pharmaceutical formulation to enter the deep lung and proceed to the preferred sites of deposition. If on the other hand the frequency spectrum of the vibratory inhaler device is ill-matched to the acoustic properties of the patient's flow-path, then coagulation and precipitation or impaction may be significantly worse, resulting in non-efficacy of the inhaled drug due to failure of the device to deliver the drug to the proper site of action.

The fluid mechanical 'resistance' of a vibratory inhaler device has been evaluated as it relates to the ability of a patient to mount an adequate inspiratory effort to achieve adequate air velocities through the device. However, little, if any, attention has been paid to the acoustic properties of vibratory inhaler dispersal mechanisms and their relationship to vocal tract acoustic spectral properties and to changes in the 'fine particle fraction' (FPF) and decreases in particle count concentration as the inhaled aerosol plume progresses into the respiratory tract.

Conventional single and multiple dose dry powder inhaler devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose. In operation, vibratory inhaler devices strive to administer a uniform aerosol dispersion amount in a desired physical form of the dry powder (such as a particulate size) into a patient's airway and direct it to a desired deposit site(s).

A number of obstacles can undesirably impact the performance of dry powder inhalers. For example, the small size of the inhalable particles in the dry powder drug mixture can subject them to forces of agglomeration and/or cohesion (certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere. Similar obstacles also affect active vibratory nebulizer devices. Further, some vibratory inhalers can retain a significant amount of the drug within the device, which can be especially problematic over time.

Some inhalation devices have attempted to resolve problems attendant with conventional 'passive' inhalers. For example, U.S. Pat. No. 5,655,523 to Hodson et al. proposes a dry powder inhalation device which has a deagglomeration/aerosolization plunger rod or biased hammer and solenoid, and U.S. Pat. No. 3,948,264 to Wilke et al. proposes the use of a battery-powered electromechanical element to vibrate the capsule to effectuate the release of the powder contained therein. These devices propose to facilitate the release of the dry powder by the use of energy input independent of patient respiratory effort. U.S. Pat. No. 6,029,663 to Eisele et al. proposes a dry powder inhaler delivery system with a rotatable carrier disk having a blister shell sealed by a shear layer that uses an actuator that tears away the shear layer to release the powder drug contents. The device also proposes a mouthpiece cover that is attached to a bottom portion of the inhaler. U.S. Pat. No. 5,533,502 to Piper proposes a powder inhaler using the patient's inspiratory effort to generating a respirable aerosol and also includes a rotatable cartridge holding the depressed wells or blisters defining the drug reservoirs. A spring-loaded carriage compresses the blister against conduits with sharp edges that puncture the blister to release the drug that is then entrained in air drawn in from the air inlet conduit so that aerosolized drug is emitted from the aerosol outlet conduit and into the patient. The published U.S. Pat. Appl No. 20070209661 of Smyth et al. also proposes a passive aeroelastic mechanism to vibrate and disperse powder using patient inspiratory efforts in a manner that is tolerant of a wide range of inspired air velocities and flow-rates. The contents of all of these patents and applications are hereby incorporated by reference as if stated in full herein. Hickey et al., in U.S. patent application Ser. No. 10/434,009 and PCT Patent Publication No. WO 01/68169A1 and related U.S. National Stage patent application Ser. No. 10/204,609, have proposed a DPI system to 'actively' facilitate the dispersion and release of dry powder drug formulations during inhalation using vibrating piezoelectric elements which may promote or increase the quantity of fine particle fraction particles dispersed or emitted from the device over conventional DPI systems. The contents of these documents are hereby incorporated by reference as if recited in full herein. Each of these active and passive inhaler devices imparts energy to the drug in order to deagglomerate it and aerosolize it, and does so with acoustic vibrations of the airstream, either directly (as the primary means of aerosolization) or indirectly (secondary to the motions of the elements involved in generation of the aerosol).

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention are generally directed to the optimization of the matching of vibratory inhaler devices to the particular anatomical and acoustic properties of the patient's mouth, pharynx, and upper respiratory tract (i.e., vocal tract), in order to achieve the most effective dispersion of a dry powder medicament (drug) using inspiratory effort of a user of the inhaler. Under transient conditions applicable to vibratory inhalers (e.g., dry powder inhalers and nebulizers), a respirable aerosolized particulate plume and airflow pattern can be generated having longitudinal acoustic waves, some of which may have frequency spectrum resonances that lead to increased (undesirable) or decreased (desirable) coagulation of drug particles during transit of the drug aerosol plume through the upper respiratory tract and deposition along the path of inspiratory flow. Time-domain acoustic reflectometric measurements are described that guide the selection of the optimal inhaler size and geometry (configuration) for each patient to assure an optimal delivery of aerosolized drug particles to the deep lung.

Accordingly, various embodiments of the present invention address the problem of undesirable agglomeration/coagulation and excessive precipitation and/or impaction of aerosolized powder particles from a vibratory inhaler in the mouth and pharynx and upper respiratory tract above the glottis of a human patient.

In one embodiment, optimization of the aerosolization and administration of an inhaled drug in dry powder form to a particular patient via a vibratory inhalation device, to thereby facilitate the aerosolization of the drug as a plume of fine particles and to inhibit the agglomeration (coagulation) of particles within the plume, in achieved. The optimization involves employing one or more measurements of acoustic frequency spectrum properties as well as one or more anatomical/geometric measurements of the structures comprising the particular patient's mouth, pharynx, and upper respiratory tract and matching a vibratory inhalation device that corresponds thereto, so as to optimize the deposition of the particulate from the inhaler in the patients deep lung and alveoli. In another aspect, the invention is directed to software systems embodiments effective in practicing the optimization.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Figure 1:
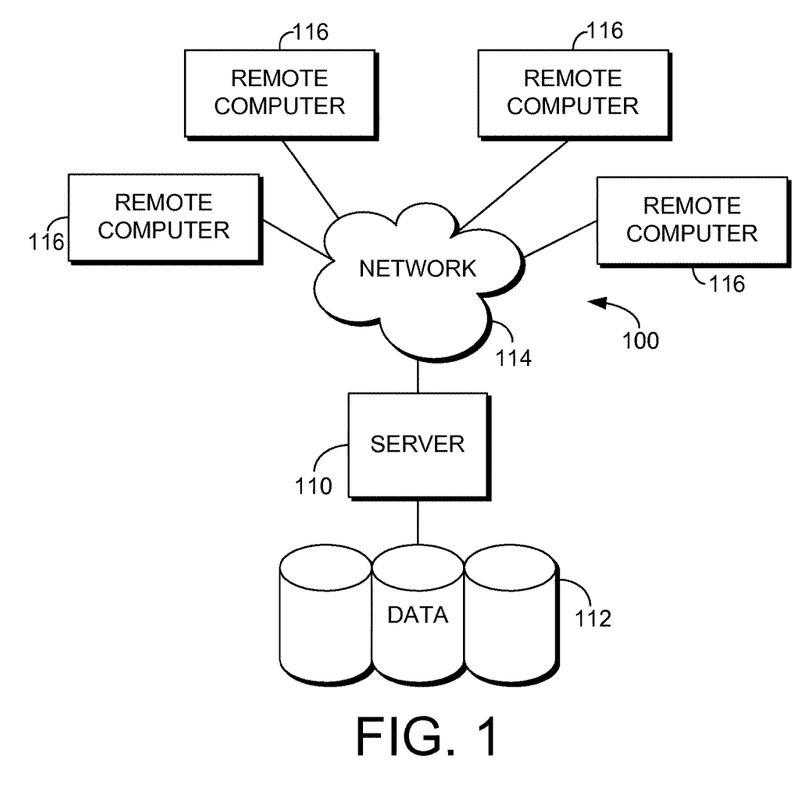
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Health data is often stored in person-centric health records, such that each individual has a health record. The term "health record" is not meant to be limited to any particular type of unified record that stores health data for an individual, examples of which include an electronic medical record (EMR), electronic health record (EHR), personal health record (PHR), continuity of care record (CCR), among others. Furthermore, the terms "patient", "individual", "person" and "subject" may be used interchangeably herein to refer to someone who has an associated health record (patient record).

As previously mentioned, embodiments of the present invention relate to optimization of the matching of vibratory inhaler devices to the particular anatomical and acoustic properties of the patient's mouth, pharynx, and upper respiratory tract, in order to achieve the most effective dispersion of aerosolized active drug particles (i.e., powder) in a respirable form, using inspiratory effort of a user of the inhaler. By respirable form, it is meant that the respirable particles are in a deaggregated form and that, upon being dispensed by an inhaler device, the particles will be dispensed so that the active agent present in the dose is in the form of particles or particle agglomerates of respirable size (preferably having a diameter between 0.5 μm and 10 μm) at the time of aerosolization and, furthermore, that the particle size distribution remains predominantly in this size range during transit through the patient's airways. The aerosolized drug in respirable form may include small agglomerates of particles, as are present in an ordered mixture, for example where the carrier material, to which the fine particles adhere. Any agglomerates present in the powder in respirable form may be broken up by the turbulence created upon actuation of the inhaler or created by the flow of the inspired air.

The respirable nature of the resultant powder may be ascertained by ACI (Anderson Cascade Impactor). In some embodiments, it is optimal for the respirable powder to have a Fine Particle Fraction (FPF) of greater than 50%. Utilizing embodiments of the present invention, a significant improvement of the FPF as compared to the FPF prior to the selection of the proper size vibratory inhaler (or flow-path modifying insert or attachment to the vibratory inhaler designed to maximize deep lung drug particle deposition. The regional deposition of drug in deep pulmonary tissues may be measured through the use of radiolabeled drug powder and quantitative gamma scintigraphy, SPECT (usually by co-spray drying with $^{99m}$Tc-DTPA), or PET (using $^{11}$C- or $^{18}$F-labeled drug), as are familiar to those practiced in the art. The latter two techniques involve short half-lives that are typically not well suited to studying dry powder inhalers, although they may be used in nebulizer and MDI and other inhaler types.

For optimal vibratory inhaler function, the step of breaking up compacted powder involves agitating the powder with force sufficient to break up the compacted powder. The force is preferably applied once the drug has been placed into a proper receptacle of the vibratory inhaler and more preferably once the receptacle has been sealed, thereby ensuring that the agitation step does not result in any appreciable loss of the measured dose of drug. Receptacles are containers, such as blisters and capsules, into which measured or metered doses of dry powder formulations are placed for storage and from which the dose of drug may be dispensed by an inhaler device.

Agitating a measured dose of a drug formulation in a sealed receptacle is accomplished by indirectly applying a vibrational force to the powder, for example, via the air within the sealed receptacle. In selecting an optimal vibratory inhaler configuration, it is contemplated that extensions or attachments or 'insert components' that can alter the geometry of the inhaler device may be considered, so as to accomplish more complete deagglomeration of the drug formulation upon inspiration by a user as well as minimize the rate of subsequent coagulation and precipitation or impaction of the particles in the upper airway and mouth.

In certain aspects, the present invention involves collecting acoustic frequency spectrum properties and anatomical/geometric measurements of the structures comprising a particular patient's mouth, pharynx, and upper airway. Time-domain acoustic reflectometry is utilized, a method that is capable not only of acquiring the necessary anatomical measurements but can assess the sensitivity to acoustic frequency spectral properties as well.

As one option, optimization of vibratory inhaler properties may be carried out using a statically configured 'spacer' or 'insert' attached to the exterior of the inhaler device so as to modify and augment the inhaler's enclosed cavity size and the geometry of the inhaler device's inspiratory airflow path, to create a flow pattern within the device that does not result in undue loss of particles within the device itself and is not associated with acoustically exacerbated agglomeration or excessive deposition of particles in the mouth or upper airway. Additionally, deagglomerating drug formulation in an inhaler device is preferably done so as to generate some acoustic emissions into the patient's airway, either directly or indirectly. For instance, employing an inhaler with a vibratory dispersal mechanism extending across at least a portion of an inspiratory flow path enables the generation of a respirable aerosol plume.

Decision-support methods, in another aspect, are also employed. The decision-support methods utilize an associative neural network (ANN), or alternatively a logistic regression statistical model, arranged so as to ascertain which inhaler device or inhaler configuration best matches the device to the patient's anatomical and upper-airway acoustic properties and thereby achieve the optimal alveolar deposition of drug.

In certain embodiments, the airflow path has a deagglomerating portion possessing a cross-sectional area that is about two centimeters squared (2 cm$^2$ or less. Additionally, in certain embodiments, the deagglomerating portion of the inspiratory airflow path can have a cross-sectional width that is about 2 cm or less and may have a length that is less than about 3 cm.

As another configuration option, a vibratory inhaler designed to maximize deep lung deposition of drug particles may include: (a) an inhaler body with an inspiratory flow path therein; and (b) at least one turbulence promoter residing in the inspiratory flow path, creating flow vortices have an axis of rotation that is substantially orthogonal to the inspiratory flow direction. Ideally, when viewed in transverse cross section, an attachment or insert extends from a bounding surface a distance into the inspiratory airflow path, the distance being a sub-portion of a cross-sectional width of the inspiratory path whereby the inhaler's vibratory mechanism deagglomerates the dry powder in response to inspiratory effort by a user.

Examples of diseases, conditions or disorders that may be treated with vibratory inhalers optimally matched to a patient's acoustic and anatomical configuration include, but are not limited to, asthma, COPD (chronic obstructive pulmonary disease), viral or bacterial infections, influenza, allergies, cystic fibrosis, and other respiratory ailments as well as diabetes and other insulin resistance disorders. Vibratory inhalers, particularly in delivering dry powder medicaments, may be used to deliver locally-acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or oligonucleotides for cystic fibrosis gene therapy may be performed.

Typical dose amounts of the unitized dry powder mixture dispersed in the inhalers may vary depending on the patient size, the systemic target, and the particular drug(s). A conventional exemplary dry powder dose amount for an average adult is less than about 50 mg, typically between about 10-30 mg and for an average adolescent pediatric subject is typically from about 5-10 mg. A typical dose concentration may be between about 1-2%. Exemplary dry powder drugs include, but are not limited to, albuterol, fluticasone, beclomethasone, cromolyn, terbutaline, fenoterol, β-agonists (including long-acting β-agonists), salmeterol, formoterol, cortico-steroids and glucocorticoids. In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. As one example, using the active dispersal systems provided by certain configurations of vibratory inhalers suggested by embodiments of the present invention, an adult dose may be reduced to under about 15 mg, such as between about 10 μg-10 mg, and more typically between about 50 μg-10 mg per puff. The active constituent(s) concentration may be between about 5-10%. In other embodiments, active constituent concentrations can be in the range of between about 10-20%, 20-40%, or even larger. In the case of nebulizer devices, the amount of drug delivered can be much larger, often hundreds of milligrams, and is achieved over a plurality of respiratory cycles or breaths instead of in just one cycle or puff.

In certain embodiments, during dose dispensing, the dry powder in a particular drug compartment or blister may be formulated in high concentrations of an active pharmaceutical constituent(s) substantially without additives (such as excipients). As used herein, 'substantially without additives' means that the dry powder is in a substantially pure active formulation with only minimal amounts of other non-biopharmacological active ingredients. The term 'minimal amounts' means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

Utilizing the methodologies of various embodiments of the present invention, vibratory inhalers may be selected to have, when analyzed in a steady state flow, at least one acoustic vibrational mode can be generated in an inspiratory flow direction in an inspiratory airflow path, as an amount of dry powder travels through the inhaler and upper respiratory tract upon patient inspiration. This facilitates deagglomeration of inhaled particles and inhibits spontaneous agglomeration (coagulation) of particles, thereby preventing trapping of undue amounts of the particles in the inhaler or in the upper respiratory tract or in the mouth during inhalation.

Accordingly, the vibratory signal can include a carrier frequency that may be between about 50 Hz to about 2000 Hz, and typically is between about 100 Hz-1000 Hz. The carrier frequency may be modified by one or more low modulating frequencies (typically between about 10-200 Hz). The frequency of the vibration can be modified to match or correspond to the flow characteristics of the dry powder substance held in a package to attempt to reach a resonant frequency(s) to promote uniform drug dispersion into the body. In some embodiments, a non-linear powder-specific dry powder vibratory energy signal comprises a plurality of selected frequencies that can be generated (corresponding to the particular dry powder(s) being currently dispensed) to output the particular signal corresponding to the dry powder(s) then being dispensed. As used herein, the term 'non-linear' means that the vibratory action or signal applied to the package to deliver a dose of dry powder to a user has an irregular shape or cycle, typically employing multiple superimposed frequencies, and/or a vibratory frequency line shape that has varying amplitudes (peaks) and peak widths over typical standard intervals (per second, minute, etc.) over time. In contrast to conventional systems, the non-linear vibratory signal input can operate without a fixed single or steady state repeating amplitude at a fixed frequency or cycle. This non-linear vibratory input can be applied to the blister to generate a variable amplitude motion (in either a one, two and/or three-dimensional vibratory motion). The non-linear signal fluidizes the powder in such a way that a powder 'flow resonance' is generated allowing active flow able dispensing. For instance, in one arrangement, a non-linear vibratory signal can include a carrier frequency that is between 1000 Hz and 40,000 Hz.

In certain embodiments, a signal of combined frequencies can be generated to provide a non-linear signal to improve fluidic flow performance. Selected frequencies can be superimposed to generate a single superposition signal (that may also include weighted amplitudes for certain of the selected frequencies or adjustments of relative amplitudes according to the observed frequency distribution). Thus, the vibratory signal can be a derived non-linear oscillatory or vibratory energy signal used to dispense a particular dry powder. In certain embodiments, the output signal used to activate the piezoelectric blister channel may include a plurality of superpositioned modulating frequencies ('overtones'; 'harmonics') and a selected carrier frequency.

Exemplary vibratory elements for an inhaler to accomplish moving dry powder into an airflow path include, but are not limited to, one or more of: (a) ultrasound or other acoustic or sound-based sources (above, below or at audible wavelengths) that can be used to instantaneously apply non-linear pressure signals onto the dry powder; (b) electrical or mechanical deflection of the sidewalls and/or floor of the inhalation flow channel and/or drug compartment, which can include magnetically induced or caused vibrations and/or deflections (which can use electro or permanent field magnets); (c) solenoids, piezoelectrically active portions and the like; (d) oscillating or pulsed gas (airstreams), which can introduce changes in one or more of volume flow, linear velocity, and/or pressure; and (e) aeroelastic films, which can apply non-linear pressure signals onto the dry powder as vibrations are passively generated by energy transferred from the patient's inspired airstream. In some particular embodiments, the vibrator may be 'active' and include one or more electrically-powered piezoelectric elements (such as a piezoceramic component, or a piezoelectric polymer film), or it may be 'passive' and include an aeroelastic element or polymer film whose motion is generated by energy of the user's inhalation inspiratory effort. Furthermore, in some embodiments, the vibratory element can be configured to vibrate the drug compartment holding the dry powder.

In one aspect, the agitation involves applying a vibrational force using a vibrational means, wherein the vibrational force is not applied directly to the receptacle at the point where the powder contacts the receptacle.

The vibrational force may be provided in the form of sonication, including acoustic and ultrasound agitation (including resonant frequency matching), shaking, impacts and percussion effects. In each case, the vibration may be applied to the outside of the sealed receptacle, and is communicated to the powder compact held inside the receptacle, preferably through the air in the receptacle (in preference to the vibration being communicated through the body of the receptacle, at least part of which will be in direct contact with the powder compact.

As those of skill in the art appreciate, various elements may be used to focus or transfer the vibrational forces, such as an acoustic lens, or transmitting media to improve contact with the sealed receptacle. Additionally, various elements may be used to apply the vibrational force may be an acoustic lens or a piezoelectric element or an aeroelastic film. Exemplary agitation techniques include applying a vibrational force to the powder in the receptacles at frequencies of less than about 1 MHz. Preferably, the frequency is from about 100 Hz to about 500 KHz, from about 1 KHz to about 200 KHz, from about 4 KHz to about 70 KHz, or from about 20 KHz to about 40 KHz. As a matter of illustration and not limitation, the agitation may be provided by contacting the filled receptacle with an ultrasonic probe, for example a probe which is operating at a frequency range of between about 1 KHz and about 200 KHz.

The amplitude of oscillation of the vibrational force is also relevant to particle movement. It has been found that application of a vibrational force with a particular amplitude to a receptacle improves the breakup of powder compacts and can assist in subsequent emptying of the receptacle.

In one aspect, the amplitude of the vibrational force should be between about 10 to about 100%, more preferably from about 50 to about 100%. Especially preferred amplitudes range from about 75 to about 100%, from about 80 to about 100%, from about 85 to about 100% or from about 90 to about 100%. Those of skill in the art would have no difficulty in ascertaining the suitable amplitude in order to break up powder compact, based upon the nature of the powder, the nature of the compacts formed during receptacle filling and the nature of the receptacle.

The pressure with which the vibrational force is applied to the receptacle has been found to be an important factor in achieving effective break up of powder compacts and improving the emptying of the receptacle upon actuation of the inhaler. Exemplary pressures include ranges from about 0.1 to about 1.5 bar, from about 0.2 to about 1.2 bar and most preferably from about 0.2 to about 0.6 bar. The value of the pressure parameter lies in its application to the enclosed environment with the patient's lips sealing the orifice of the inhaler, through which the inspired jet of air is drawn.

Finally, the duration for which the vibrational force applied to the receptacle has been found to also be an important factor in achieving effective break up of powder compacts and improving the emptying of the receptacle.

It has been found that optimal results are achieved if the vibrational force is applied for between about 0.10 and 5 seconds. The vibrational force should be applied for long enough to allow complete break up or deaggregation of the compacted powder, but must not be so long as to have any detrimental effects on the powder, for example by causing ordered mixtures to segregate. Preferably, the vibrational force is applied for between about 0.25 to about 1 second. The duration may need to be adjusted, depending upon the other parameters. For example, a lower frequency vibrational force may need to be applied for longer in order to have the desired effect.

Figure 2:
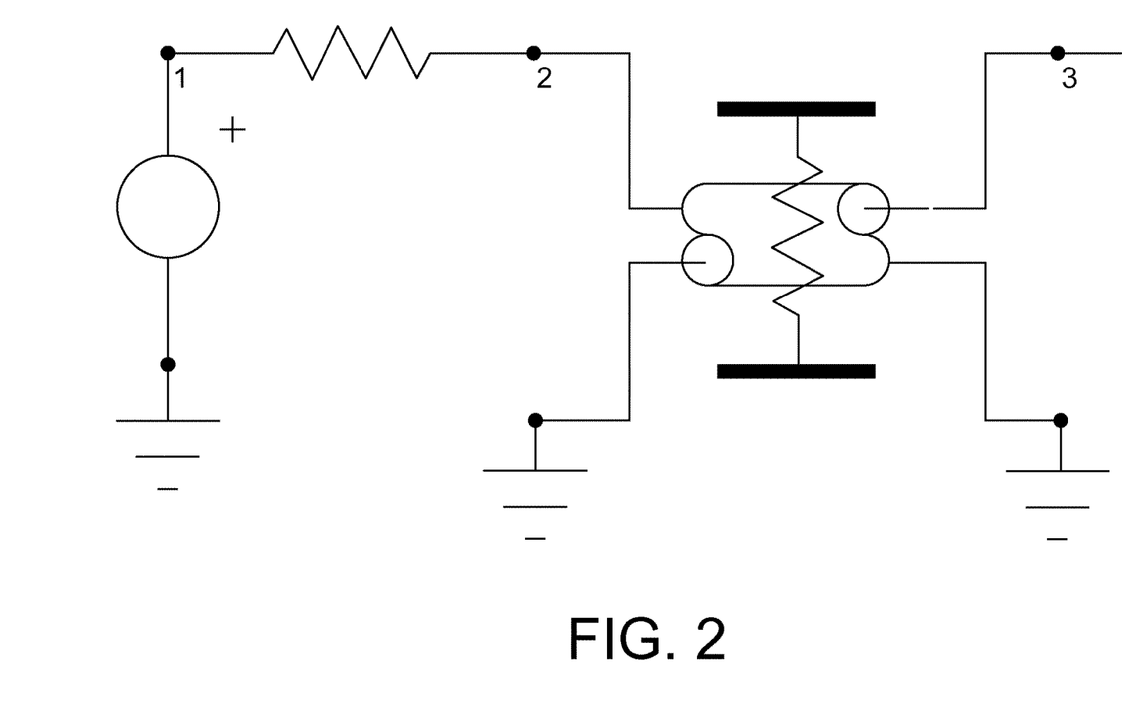
FIG. 2 is a circuit diagram modeling a human's upper airway as a lumped-parameter transmission line, using SPICE (Simulation Program with Integrated Circuit Emphasis) software to solve electrical-analog differential equation model.

Turning now to FIG. 2, a circuit diagram is utilized to model a human's upper airway (from lips to glottis) as a lumped-parameter transmission line, using SPICE (Simulation Program with Integrated Circuit Emphasis) software to solve electrical-analog differential equation model.

Figure 3:
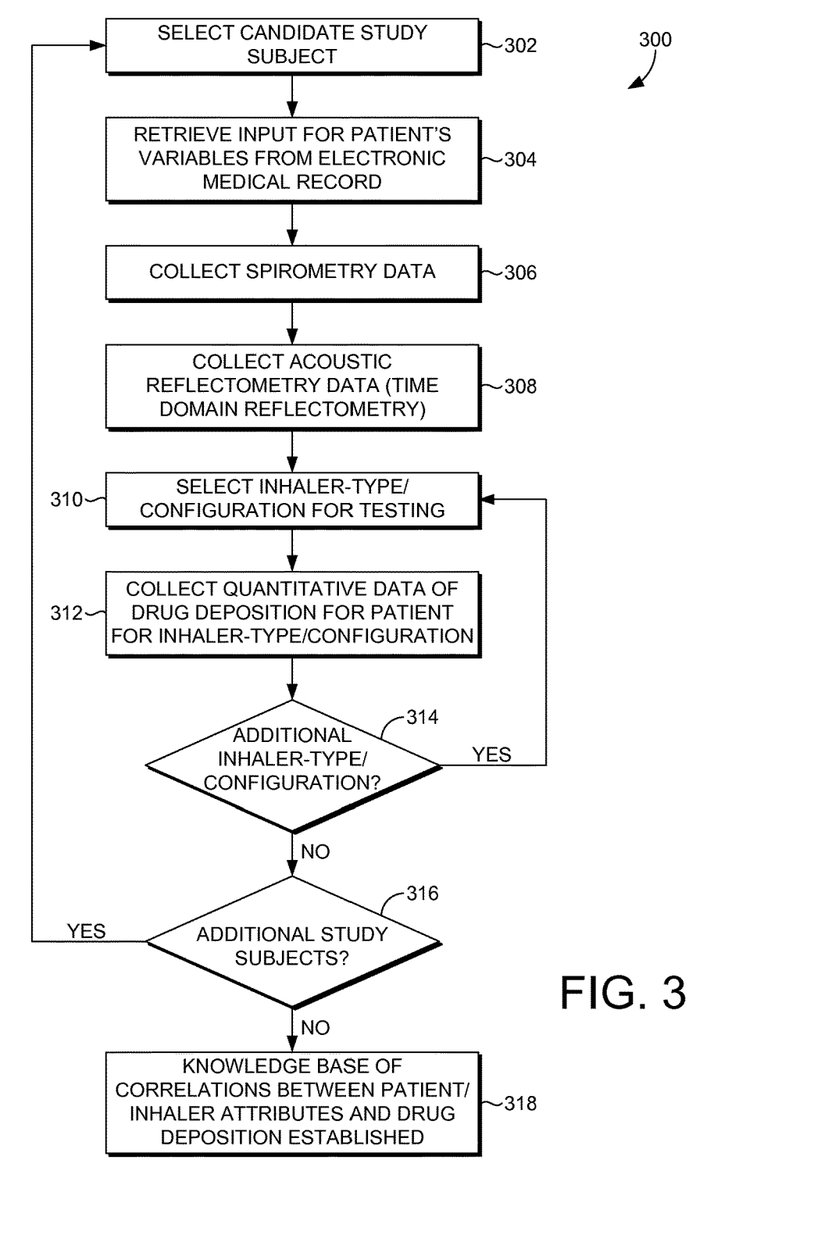
FIG. 3 is a flow diagram showing a method for establishing a knowledge base correlating patient and inhaler attributes with deep lung drug deposition in accordance with an embodiment of the present invention.

With respect to FIG. 3, a flow diagram is provided that illustrates a method 300 for establishing a knowledge base correlating patient and inhaler attributes with deep lung drug deposition. The knowledge base will also associate patient demographic, spirometric, and laryngometric attributes with quantitative percentage deposition of radiolabelled test aerosol particles (as one example, $^{99m}$Tc-DTPA lactose) in the deep lung. Accordingly, at block 302, a prospective candidate for study (a subject) is screened, consented, and selected. At block 304, demographic variables such as age, gender, height, and other parameters such as are routinely recorded in the patient's electronic medical record are retrieved for the subject.

Thereafter, at block 306, quantitative spirometry is performed on the subject and, at a minimum, forced expiratory volume 1-second (FEV1), forced vital capacity (FVC), and FEV1 as a percent of FVC are measured or calculated. At block 308, time-domain acoustic reflectometric laryngometry is performed on the subject, and, at a minimum, the distance to the point of maximal narrowing (Lmin), the distance to the glottis (Lglot), and the maximal airway area (Amax) are measured, preferably with time-domain reflectometry acoustic frequency spectrum in the same range as frequencies emitted by the relevant alternative inhaler/nebulizer (vibratory inhaler) devices. For instance a TDR apparatus available from Sleep Group Solutions Inc. of North Miami Beach, Fla. was employed in one implementation. However, similar clinical acoustic TDR devices could likewise be used.

At block 310, one of a plurality of relevant inhaler types and configurations (e.g., with or without spacer, with spacers of different length and bore, etc.) is selected for testing. At block 312, quantitative 2-dimensional or 3-dimensional scintigraphy is performed following the subject's inhaling radiolabelled test aerosol using the selected inhaler device. Associated scattering corrections and integration of pixel/voxel intensities is performed to calculate percentage dose deposition in deep lung locations. Data is captured from blocks 304 to 312 in the knowledge base.

At block 314, after a suitable time has elapsed (depending on the half-life of the radionuclide used for the foregoing scintigraphy) a determination is made as to whether to repeat the study on the same subject using a different inhaler type or inhaler configuration. If so, then the method returns to block 310 and the process of selecting an inhaler type/configuration is repeated. Otherwise, if the study is not to be repeated on the subject at this time, then it is determined at block 316 whether additional study subjects should be examined in building the knowledge base. If so, then the method returns to block 302 where a candidate study subject is selected and the process repeated. Otherwise, if no additional study subjects are to be examined, then, at block 318, the knowledge base of correlations between patient and inhaler attributes and drug particular deposition is established.

Figure 4A:
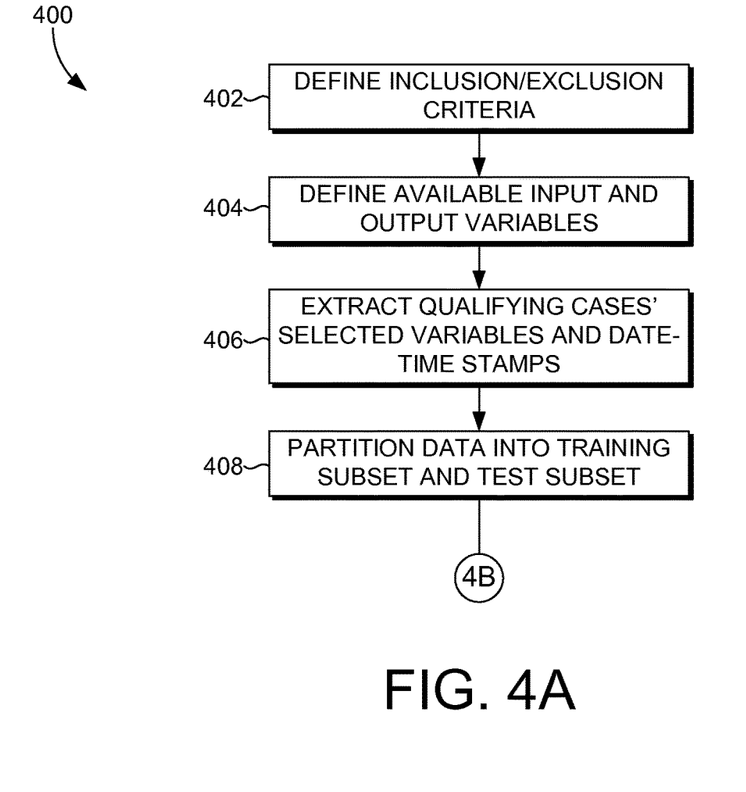
FIGS. 4A and 4B include a flow diagram showing a method for producing and validating a statistical model for accurately predicting patient attributes that match given inhaler attributes to achieve deep lung drug deposition in accordance with an embodiment of the present invention.
Figure 4B:
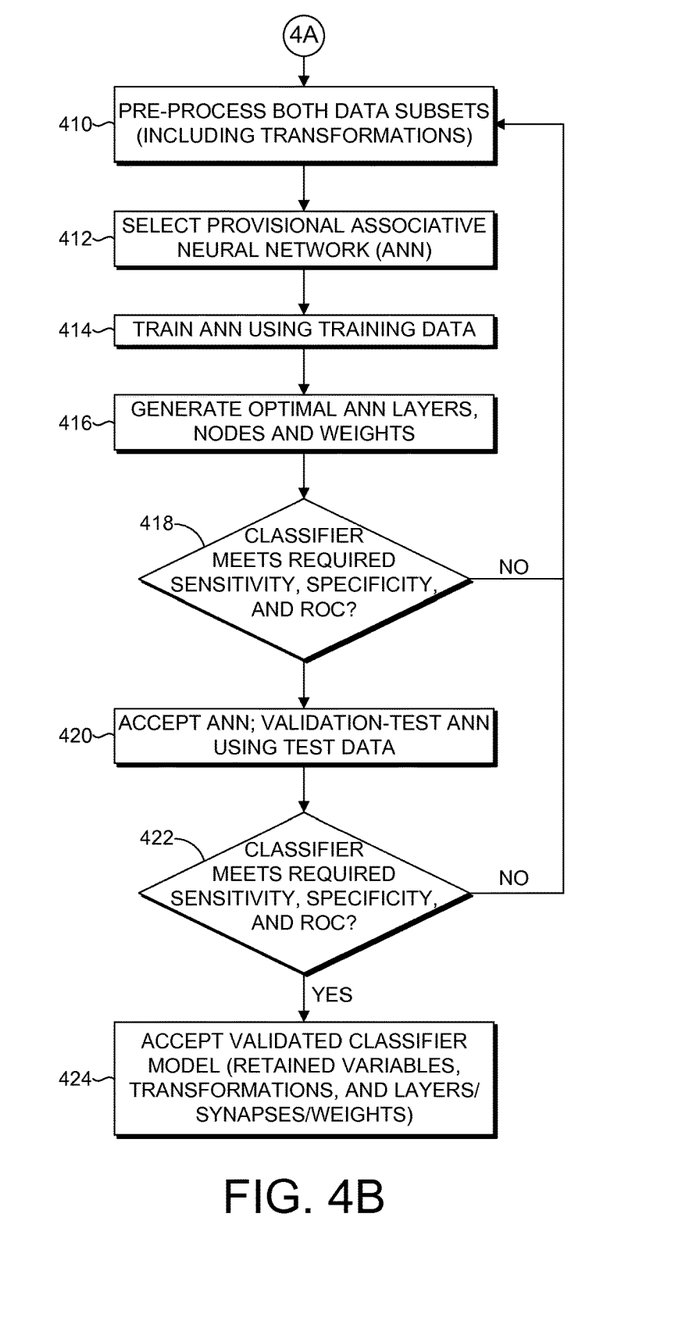

Turning to FIGS. 4A and 4B, a flow diagram is provided that illustrates a method 400 for producing and validating a statistical model for accurately predicting patient attributes that match given inhaler attributes to achieve deep lung drug deposition in accordance with an embodiment of the present invention. In the particular embodiment illustrated, the statistical model employs a predictive neural network, with the data acquired in the knowledge base according to method 300. However, those of skill in the art appreciate that the statistical model may employ logistic regression as a matter of design choice, within method 400.

Initially, inclusion-exclusion criteria is defined, as shown at block 402, as well as problem specification in terms of available input and output variables, at block 404. producing and validating a statistical model for accurately predicting patient attributes that match given inhaler attributes to achieve deep lung drug deposition Thereafter, as shown at block 406, training data is collected. Training data comprises a set of data points having known characteristics. This data may come from research facilities, academic institutions, commercial entities, and/or other public or confidential sources The collection of training data may be accomplished manually or by way of an automated process, such as known electronic data transfer methods. Accordingly, an exemplary embodiment of the learning machine for use in conjunction with the present invention may be implemented in a networked computer environment.

With reference again to block 402, it is known to those practiced in the art that to construct an effective classifier, appropriate inclusion-exclusion criteria is first defined in sufficient detail that the cases acquired for the purpose of classifier design accurately represent the population to which the classifier is intended to be applied.

With reference again to block 404, for the cohort meeting the applicable inclusion-exclusion criteria, database retrieval of extant electronic medical records is performed. This serves to define the available input and output clinical and laboratory variables and characterize the descriptive statistics of each variable and assess the degree of "missingness" of information for each variable. In one embodiment, variables whose values are missing at a greater than 20% rate are excluded from subsequent consideration in classifier construction and development. It should be understood that although database retrieval of electronic medical records is described, any type of patient medical or health record may be utilized within the various embodiments of the present invention (in the context of method 400 or in other contexts of embodiments of the present invention).

Next, at block 406, information for the qualifying cases for each of the selected variables is extracted from the electronic medical record or other data source, including the date-time stamp for each item. As shown at block 408, the retrieved cases and case information are partitioned into two subsets—a first subset that is to be utilized for classifier construction and training (training data subset), and a second subset that is to be used for classifier validation testing (test data subset). Any of a variety of partitioning methods can be employed such as are well-known to statisticians practiced in the art. Randomized 'bootstrap' sampling without replacement, for example, may be used to insure that the subsets that are generated are not biased with regard to time, source institutions, or other factors. In some embodiments, the partitioning is made into two subsets of equal size (50%-50%). However, there is no requirement that this be the case. The subsets can be of different sizes. In some embodiments, the sample size of each subset is sufficient to achieve a desired 80% or greater statistical power for classification of the cases.

As shown at block 410, statistical pre-processing is performed, including calculation of mean, median, standard deviation, skewness, and kurtosis for each of the numerical variables and frequency tables for each of the categorical variables. In instances where the statistical distribution of a numerical variable is markedly skewed, then logarithmic or power-law or other transformation of that variable is performed by methods that are well-known to statisticians, so as to produce a distribution for the transformed variable that is symmetrical and more nearly Gaussian in shape than that of the raw variable. The collected training data is optionally pre-processed in order to allow the learning machine to be applied most advantageously toward extraction of the knowledge inherent in the training data. During this preprocessing stage, a variety of different transformations can be performed on the data to enhance its usefulness. Such transformations, examples of which include addition of expert information, spline conversion, logarithmic or power-law transformations, etc., will be readily apparent to those of skill in the art. However, the preprocessing of interest in an embodiment of the present invention is the reduction of dimensionality by way of feature selection.

The resulting dataset is processed with associative neural network (ANN), as shown at block 412. The training data subset is used to condition the ANN coefficients and generate ANN layers, nodes and weights (at block 416) that optimally distinguish the cases according to the dependant variable.

As shown at block 414, the ANN is trained using the pre-processed data from the training data subset. Accordingly, the ANN is trained by adjusting its operating parameters until a desirable training output is achieved. The determination of whether a training output is desirable may be accomplished either manually or automatically by comparing the training output to the known characteristics of the training data. The ANN is considered to be trained when its training output is within a predetermined error threshold from the known characteristics of the training data.

At block 418, the resulting classification table is examined by available receiver-operating characteristic (ROC) statistical methods, to assess whether the classifier generated by the ANN meets the design requirements established for the predictive model. In the event that ROC is lower than the acceptable minimum (e.g., a minimum ROC area-under-the-curve (C-statistic) of a particular value was not met), then additional iterations through blocks 310-318 are performed. Alternatively, if ROC is acceptable at block 418, then the ANN is accepted and the model is validation-tested, as shown at block 420, using the test data subset that was previously prepared and reserved at block 408.

Based on the post-processed test output, it is determined through block 422 whether an optimal minimum was achieved by the trained ANN. If it is determined that the optimal minimum has not been achieved by the trained ANN at block 322, then the method returns to block 410, and ANN selection is readjusted (blocks 410-420). When it is determined in step 422 that the optimal minimum has been achieved, the validated classifier model is accepted for implementation, at block 424.

Figure 5:
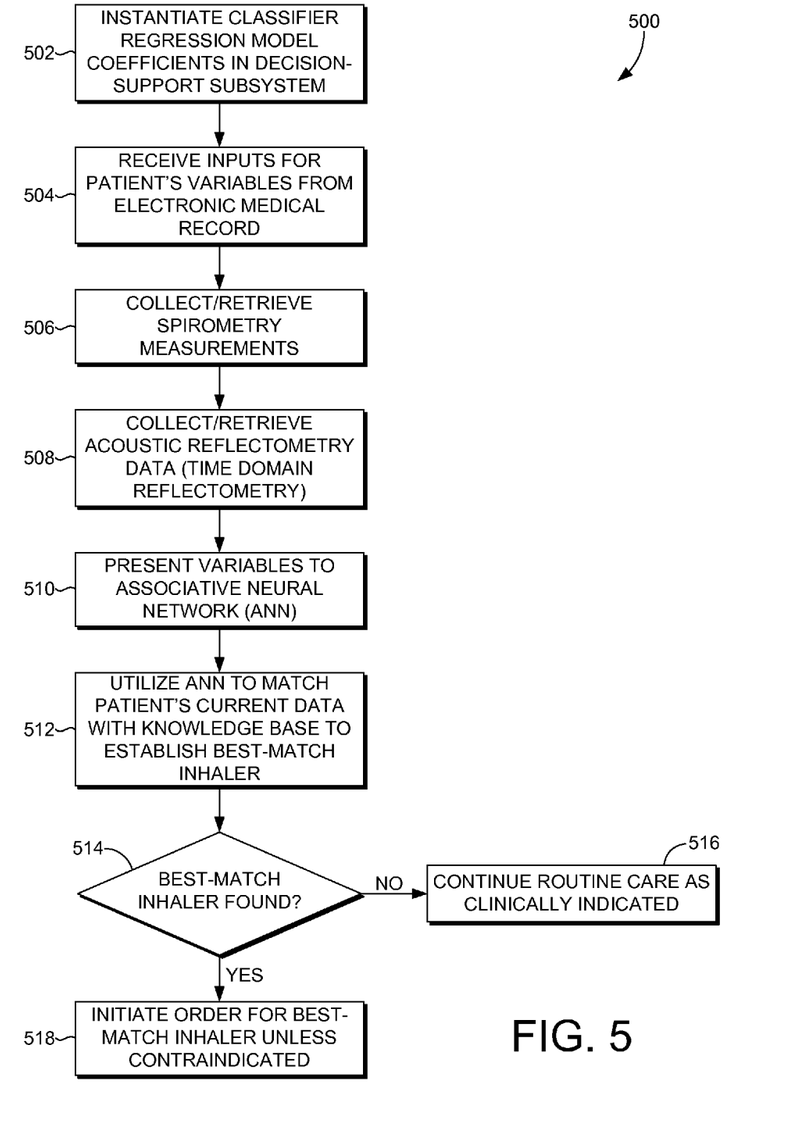
FIG. 5 is a flow diagram showing a method for prospectively predicting a patient-inhaler match for deep lung drug deposition employing a statistical model in accordance with an embodiment of the present invention.

With respect to FIG. 5, a flow diagram is provided that illustrates an exemplary method 500 for prospectively predicting a patient-inhaler match for deep lung drug deposition employing a statistical model. Accordingly, a ideal inhaler type or configuration is suggested that will be most likely to achieve optimal (high-percentage) delivery of aerosolized drug particles to the respiratory alveoli. The method 500 begins in block 502, where the ANN classifier and its model coefficients are instantiated in a decision-support subsystem (DSS), such as a DSS integrated with an electronic medical record of the patient, as is known to those of skill in the art. At block 504, the required demographic and clinical variables' values are retrieved from the patient's medical record. Alternatively, in another embodiment, the statistical model is deployed in standalone software, either on an internet web portal, for instance in JAVA or ASP application software, or in a portable device such as a PDA or cellphone. In these embodiments, the user provides the input data for the inhaler type/configuration matching to occur. In either case, the decision-support subsystem receives input information for each of the classifier variables.

At block 506, if spirometry data have not already been contemporaneously acquired, then a new spirometry procedure is conducted and data entered. Otherwise, recent FEV1, FVC, and FEV1% FVC values can be retrieved from the medical record and loaded into the DSS. At block 508, if acoustic reflectometry data (TDR) have not already been contemporaneously acquired, then a new acoustic reflectometry (TDR) procedure is performed and data entered. Otherwise, recent Lmin, Lglot, and Amax values can be retrieved from the medical record and loaded into the DSS. At block 510, any newly-acquired spirometry and/or acoustic reflectometry data are stored in the medical record, and the set of patient variables is presented to the ANN. At block 512, the ANN algorithm computes the matching of the current patient's data to the previously acquired knowledge base of test subject demographic, clinical, spirometric, acoustic reflectometry (TDR), and scintigraphic data. A Hopfield network or other pattern-recognition neural network may be utilized, as will be apparent to those knowledgeable in the field of the invention. As one example, an ANN implemented in Java using the open-source JOONE software environment was utilized. However, any of a variety of neural network software packages would serve equally well for this purpose. The output of the ANN algorithm identifies one or a plurality of the closest matches and the associated percent-deep-lung deposition values. A determination is then made in step 514 as to whether a preferable match of patient to inhaler is found, based on the output. If a preferable match is found, then at block 518, the clinician (e.g., prescribing physician) is then able to initiate an order or prescription for the device or configuration that is optimal for the individual and likeliest to achieve an optimal delivery of aerosolized drug to the alveoli. Alternatively, if a preferable match is not found, then at block 516, routine care is continued as clinically indicated.

Figure 6:
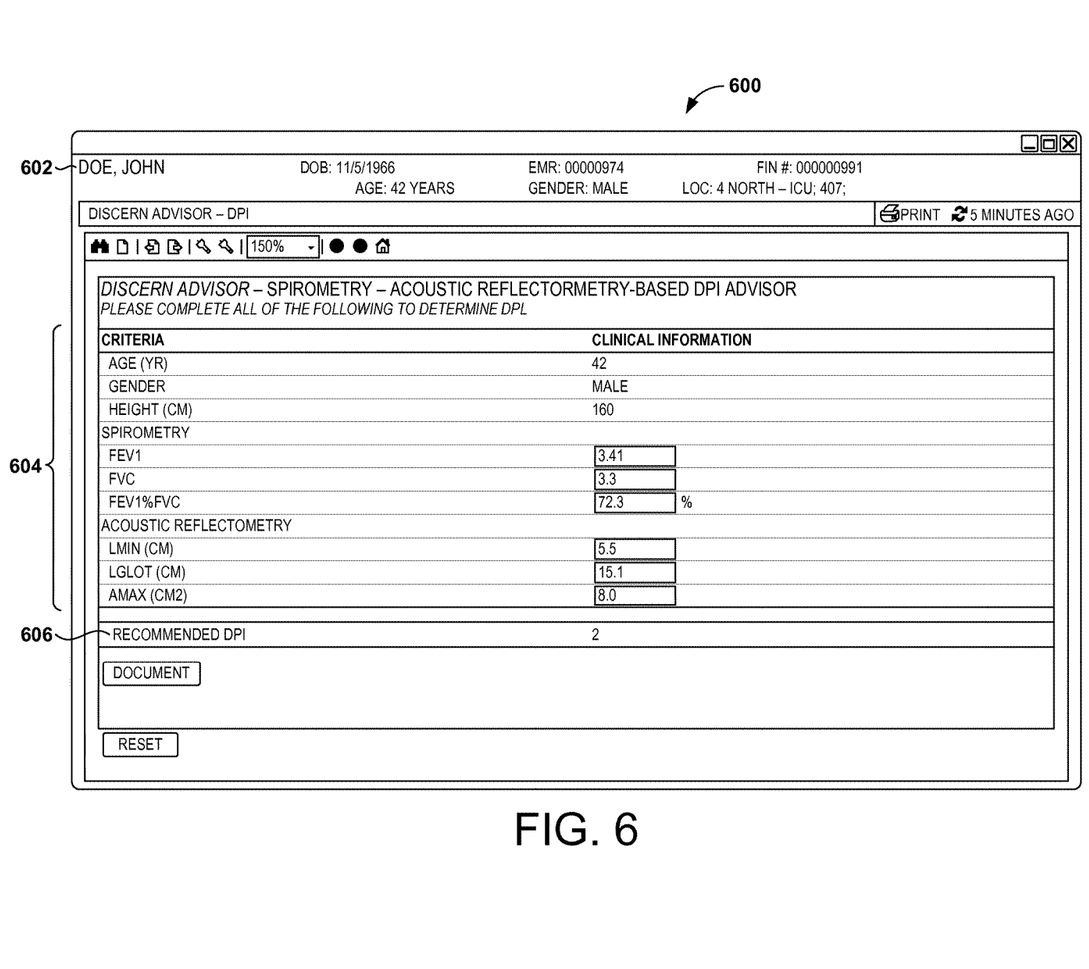
FIG. 6 is an illustrative screen display of an exemplary view for an electronic form which receives and retrieves the necessary variables' values and determines a recommended vibratory inhaler based on a statistical model employed in accordance with an embodiment of the present invention.

An embodiment of the present invention will now be described with reference to FIG. 6, which illustrates an exemplary screen display 600 providing information regarding an electronic form which receives and retrieves the necessary variables' values and determines a recommended vibratory inhaler based on a statistical model. It will be understood and appreciated by those of ordinary skill in the art that the screen display of FIG. 6 is provided by way of example only and is not intended to limit the scope of the present invention in any way.

As shown in FIG. 6, the screen display 600 includes a patient information area 602 proving general information regarding the patient currently being evaluated, including the patient's name, age, date of birth, gender, and other general patient information.

The screen display also includes a decision support patient criteria area 604. The patient criteria area 604 allows a clinician to enter the input data set that is used in conjunction with the statistical model developed, for instance, using the method 400 described above with reference to FIGS. 4A and 4B to generate a best match inhaler type or configuration. In the present example, the patient criteria area 604 includes variables that relate to spirometry and acoustic reflectometry measurements, as well as certain patient demographics retrieved from the medical record (e.g., age, gender, height). Although FIG. 6 illustrates a screen display in which a clinician enters certain data values for the displayed variables in the patient criteria area 604, in embodiments of the present invention, all or a portion of the values may be populated automatically by the system retrieving the values from an electronic medical record for the newborn.

The screen display 600 also displays information 606 regarding the recommended vibratory inhaler, in this case a dry powder inhaler (DPI), determined based on the input data in the patient criteria area 604 and utilizing the statistical model, in this case the associative neural network (ANN). The recommended inhaler in this case, having certain physical and acoustic properties, is associated with an integer number. Each variation in vibratory inhaler type and configuration recommended is therefore associated with a unique integer number. However, those of skill in the art appreciate that other identification systems (besides integers) may be utilized to reference various inhaler types and configurations suitable for recommending to persons with a variety of respiratory tract acoustic and physiological configurations.

Exemplary System Implementation

Multi-variable pattern matching, logistic regression, discriminant analysis, cluster analysis, decision-tree induction, or other methods known to those skilled in the art are utilized to establish, for each inhaler device model and configuration, the correlations between upper respiratory tract acoustic variables, spirometry respiratory physiologic variables, patient demographic variables, and the percentage deposition of drug powder particles in the deep lung as measured by quantitative nuclear medicine imaging such as gamma scintigraphy, SPECT, or PET. In one embodiment, the statistical predictive model utilizes the following variables: patient age in years, gender, height in cm, FEV1 in L, FVC in L, FEV1/FVC ratio as %, the distance from the incisor teeth to the first minimum airway cross-section in cm, and the maximum areal dimension in the mouth/oropharynx in square centimeters ($cm^2$) as measured by acoustic reflectometry data.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. A method of optimizing an aerosolization and administration of an inhaled drug to a patient via a vibratory inhaler device to facilitate the aerosolization as a plume of fine particles and to inhibit agglomeration or coagulation of particles within the plume, the method comprising:

collecting time-domain response measurements by performing acoustic pulse reflectometry on a patient, the time-domain response measurements collected corresponding to acoustic and anatomical properties associated with the patient's mouth, pharynx, and upper airway;

identifying a frequency spectrum of acoustic vibrations that are specific to the patient's mouth, pharynx, and upper airway, wherein the frequency spectrum identified is based on the time-domain response measurements collected by performing acoustic pulse reflectometry on the patient; and identifying a vibratory inhaler device having a first dispersal configuration, wherein the vibratory inhaler device having the first dispersal configuration is specifically identified based on a determination that the first dispersal configuration produces the frequency spectrum of acoustic vibrations that are specific to the patient's mouth, pharynx, and upper airway, wherein the first dispersal configuration includes a size of the vibratory inhaler device and a geometry of the vibratory inhaler device.

2. The method of claim 1, wherein identifying a vibratory inhaler device having the first dispersal configuration that produces the frequency spectrum of acoustic vibrations that are specific to the patient's mouth, pharynx, and upper airway further comprises identifying the first dispersal configuration based on predetermined data for a plurality of vibratory inhaler devices, each of the plurality of vibratory inhaler devices having at least one dispersal configuration, the predetermined data including at least one of inhaler fine particle fraction data and pulmonary drug deposition data.

3. The method of claim 2, wherein the plurality of vibratory inhaler devices have a variety of geometries, resistance to airflow, and other physical properties.

4. The method of claim 1, wherein the vibratory inhaler device comprises a dry powder inhaler or a dry powder nebulizer.

5. The method of claim 2, further comprising matching the frequency spectrum of acoustic vibrations that are specific to the patient's mouth, pharynx, and upper airway with the predetermined data for at least one of the plurality of vibratory inhaler devices.

6. The method of claim 2, wherein the predetermined data includes one or more of (1) the at least one dispersal configuration of each of the plurality of vibratory inhaler devices, (2) a frequency spectrum produced by the at least one dispersal configuration of each of the plurality of vibratory inhalers, and (3) a deep lung drug deposition rate.

7. The method of claim 6, wherein the predetermined data further includes one or more of demographic, spirometric, and laryngometric attributes associated with the patient.

8. Non-transitory computer readable media having computer-executable instructions embodied thereon that, when executed, perform a method for identifying an optimal configuration of a vibratory inhaler device for a patient, the method comprising:

collecting time-domain response measurements by performing acoustic pulse reflectometry on a patient;

storing the time-domain response measurements of the patient as acoustic reflectometry data in a medical record of the patient;

identifying a frequency spectrum of acoustic vibrations that are specific to the acoustic reflectometry data corresponding to the patient and spirometry data corresponding to the patient; and selecting a vibratory inhaler device having a first dispersal configuration, wherein the vibratory inhaler device having the first dispersal configuration is selected based on a determination that the first dispersal configuration produces a frequency spectrum that matches (i) the frequency spectrum of acoustic vibrations that are specific to the acoustic reflectometry data corresponding to the patient and (ii) the spirometry data corresponding to the patient, wherein the first dispersal configuration increases deep-lung drug deposition rates in the patient based on the matching frequency spectrum produced via the first dispersal configuration, wherein the first dispersal configuration includes a size of the vibratory inhaler device and a geometry of the vibratory inhaler device; and initiating an order of the vibratory inhaler device having the first dispersal configuration for the patient.

9. The media of claim 8, wherein the first dispersal configuration further produces a resonance that corresponds to a decreased coagulation of drug particles released from the vibratory inhaler device.

10. The media of claim 8, storing the time-domain response measurements of the patient as acoustic reflectometry data in a medical record of the patient includes updated a medical record of the patient.

11. The media of claim 10, wherein the medical record data comprises age, gender, and height.

12. The media of claim 8, wherein the acoustic reflectometry data further includes at least one of anatomical measurements and geometric measurements associated with the patient's mouth, pharynx, and upper airway.

13. The media of claim 12, wherein the at least one of the anatomical measurements and the geometric measurements includes a maximum areal dimension in a mouth of the patient.

14. The media of claim 12, wherein an associative neural network performs the identifying the configuration of the vibratory inhaler device as an optimal configuration for the patient.

* * * * *